USOO6135773A

United States Patent [19]
Lazzara

[11] Patent Number: 6,135,773
[45] Date of Patent: Oct. 24, 2000

[54] SINGLE TOOTH ALIGNMENT SYSTEM

[75] Inventor: Richard L. Lazzara, Lake Worth, Fla.

[73] Assignee: Implant Innovations, Inc., Palm Beach Gardens, Fla.

[21] Appl. No.: 09/014,067

[22] Filed: Jan. 27, 1998

Related U.S. Application Data

[60] Provisional application No. 60/036,288, Jan. 27, 1997.

[51] Int. Cl.$^7$ .................................................. A61C 11/00
[52] U.S. Cl. ........................................... 433/213; 433/173
[58] Field of Search ................................. 433/172, 173, 433/174, 175, 176, 213, 214

[56] References Cited

U.S. PATENT DOCUMENTS

| | | | |
|---|---|---|---|
| 4,086,701 | 5/1978 | Kawahara et al. ........................ | 32/10 |
| 4,758,161 | 7/1988 | Niznick ................................... | 433/173 |
| 4,842,518 | 6/1989 | Linkow et al. .......................... | 433/174 |
| 4,850,870 | 7/1989 | Lazzara et al. ......................... | 433/174 |
| 4,850,873 | 7/1989 | Lazzara et al. ......................... | 433/220 |
| 4,856,994 | 8/1989 | Lazzara et al. ......................... | 433/173 |
| 4,955,811 | 9/1990 | Lazzara et al. ......................... | 433/173 |
| 4,988,298 | 1/1991 | Lazzara et al. ......................... | 433/173 |
| 5,000,685 | 3/1991 | Brajnovic ................................ | 433/173 |
| 5,006,069 | 4/1991 | Lazzara et al. ......................... | 433/173 |
| 5,015,186 | 5/1991 | Detsch .................................... | 433/173 |
| 5,030,096 | 7/1991 | Hurson et al. .......................... | 433/173 |
| 5,035,619 | 7/1991 | Daftary .................................... | 433/173 |
| 5,040,983 | 8/1991 | Binon ...................................... | 433/173 |
| 5,071,351 | 12/1991 | Green, Jr. et al. ...................... | 433/173 |
| 5,073,111 | 12/1991 | Daftary .................................... | 433/173 |
| 5,100,323 | 3/1992 | Friedman et al. ....................... | 433/173 |
| 5,125,841 | 6/1992 | Carlsson et al. ........................ | 433/172 |
| 5,135,395 | 8/1992 | Marlin ..................................... | 433/174 |
| 5,145,371 | 9/1992 | Jorneus ................................... | 433/173 |
| 5,145,372 | 9/1992 | Daftary et al. .......................... | 433/173 |
| 5,188,800 | 2/1993 | Green, Jr. et al. ...................... | 422/23 |
| 5,209,659 | 5/1993 | Friedman et al. ....................... | 433/173 |
| 5,209,666 | 5/1993 | Balfour et al. .......................... | 433/173 |
| 5,213,502 | 5/1993 | Daftary .................................... | 433/172 |
| 5,281,140 | 1/1994 | Niznick ................................... | 433/172 |
| 5,292,252 | 3/1994 | Nickerson et al. ...................... | 433/173 |
| 5,297,963 | 3/1994 | Daftary .................................... | 433/172 |
| 5,334,024 | 8/1994 | Niznick ................................... | 433/173 |
| 5,336,090 | 8/1994 | Wilson, Jr. et al. ..................... | 433/172 |
| 5,338,196 | 8/1994 | Beaty et al. ............................. | 433/172 |
| 5,431,567 | 7/1995 | Daftary .................................... | 433/172 |
| 5,433,606 | 7/1995 | Niznick et al. ......................... | 433/173 |
| 5,662,476 | 9/1997 | Ingber et al. ........................... | 433/213 |
| 5,674,073 | 10/1997 | Ingber et al. ........................... | 433/173 |
| 5,813,858 | 9/1998 | Singer ..................................... | 433/173 |

FOREIGN PATENT DOCUMENTS

| | | |
|---|---|---|
| 0 442 855 A1 | 8/1991 | European Pat. Off. . |
| 1911470 | 10/1972 | United Kingdom . |

OTHER PUBLICATIONS

Exhibit A, a drawing of a healing abutment.
Exhibit B, an assembly drawing of a coping and the component drawings which comprise the coping assembly.

(List continued on next page.)

*Primary Examiner*—Ralph A. Lewis
*Attorney, Agent, or Firm*—Arnold White & Durkee

[57] ABSTRACT

A method and set of components is disclosed for positioning an implant analog within a dental impression taken from the patient, relative to the position of a dental implant or "converted" implant in the patient's mouth. The set of components include an implant orientation tool, an impression coping and an implant analog having an orientation reference. The method involves the steps of attaching an impression coping to the implant and making a dental impression. An interlocking member of the impression coping is accessible through an opening in the impression material. The implant analog is then attached to the impression coping. The implant analog is positioned by rotating it in the coping until the orientation reference on one end of the implant analog reaches an alignment position mirroring the alignment position of the implant itself. This is achieved by attaching the orientation tool to the interlocking member of the implant, noting the position of the orientation reference of the orientation tool, and rotating the implant analog in the impression material until the orientation reference of the implant analog mirrors the orientation of the orientation tool.

10 Claims, 16 Drawing Sheets

OTHER PUBLICATIONS

Lewis, S.G. et al., Single Tooth Implant Supported Restorations, Intnatl. Jrnl. of Oral & Maxillofacial Implatns, vol. 3, No. 1, pp. 25–30, 1988.

Lewis, S.G. et al.,The "UCLA" Abutment, Intnatl. Jrnl. of Oral & Maxillofacial Implants, vol. 3, No. 3, pp. 183–189, 1988.

Perri DDS, George et al., *Single Tooth Implants,* CDA Journal, vol. 17, No. 3, March 1989.

DIA™ Dental Imaging Associates, Implanted—The Source, "The Anatomical Abutment System", Copyright Date Oct. 9, 1991 on p. 10. (Front Cover, pp. 1–10 and Back Cover).

Steri–Oss®, Product Catalog, Feb. 1992, Cover Page, pp. 7, 14, and Last Page.

Branemark System (Nobelpharma), Product Catalog Prosthetics, 1991, 24 pages.

Steri–Oss®, Product Catalog, Sep. 1990, 36 pages.

IMTEC Hexed–Head™ Implant System, Spring 1993 Catalog, 15 pages.

Interpore International, IMZ™ Prosthetic Flow Chart, Jul. 1993, 2 sheets.

Impla–Med. Catalog, Mar. 1991, 16 pages.

Stryker Dental Implants, Catalog Data Sheets, Undated, 4 sheets.

Stryker Dental Implants, Price List, Jun. 1, 1993, 46 pages.

Oratronics, Inc., "Options for Oral Implantology . . . Oratronics Endosseous Tri–Dimensional T–3D Oral Implant Healing System (OIHS)", 1978 8 pages.

Bio–Esthetic™ Abutment System Technique Manual Steri–Oss, Inc., 1995, 6 pgs.

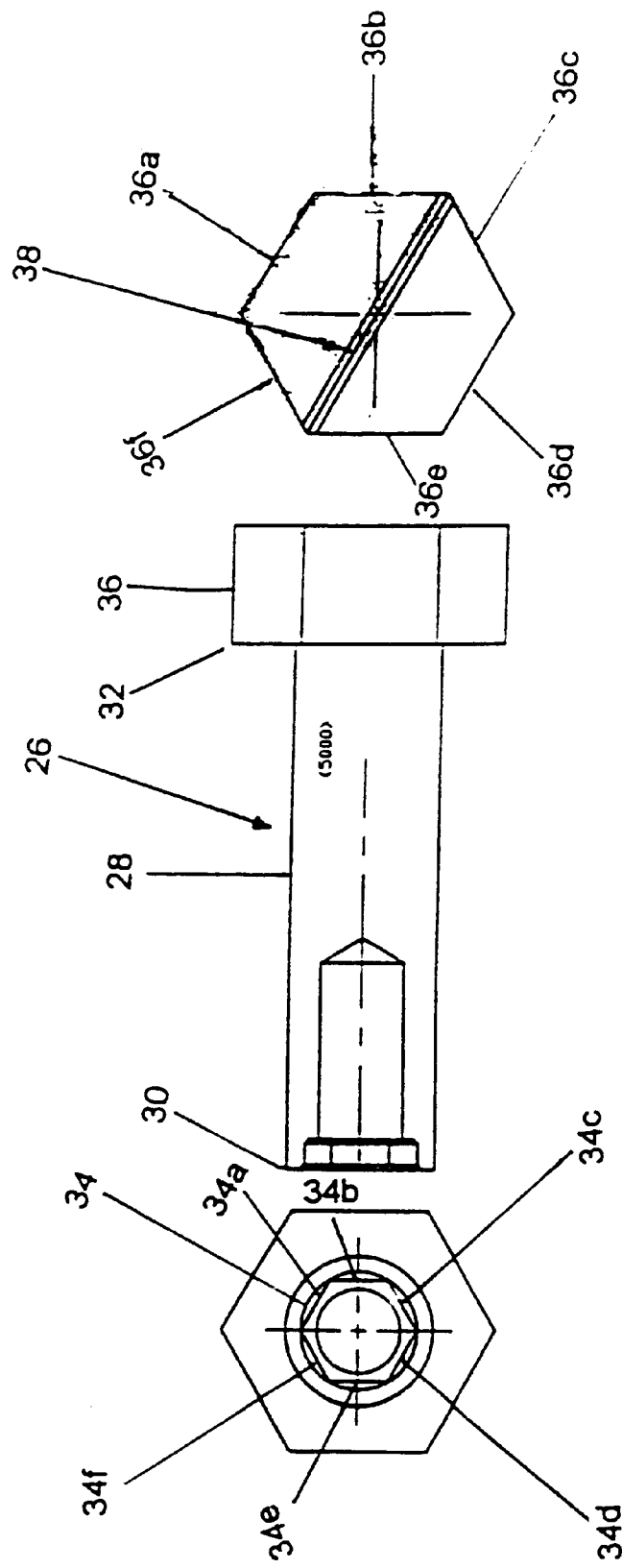

SINGLE TOOTH ALIGNMENT SYSTEM

CROSS REFERENCES To RELATED APPLICATIONS

This application claims the priority of copending Provisional Patent Application Ser. No. 60/036,288, filed Jan. 27, 1997.

FIELD OF THE INVENTION

The present invention relates generally to dental restoration systems wherein a prosthodontic restoration simulating the appearance of a natural tooth is attached to a dental implant imbedded in the jawbone of a dental patient. More particularly, the present invention is directed to devices and a method for aligning the implant and for ensuring that the prosthodontic restoration is fashioned in proper orientation with adjacent teeth.

BACKGROUND OF THE INVENTION

Dental implants are becoming an increasingly popular means for restoring lost teeth in wholly or partially edentulous patients. A dental implant typically comprises a threaded titanium cylinder having a length ranging between about 5 mm and 18 mm and a diameter ranging between about 3 mm and 6 mm. Dental implants normally include an interlocking member at their gingival end for anti-rotationally connecting with a cooperating surface of a prosthodontic restoration (i.e. artificial tooth) or restoration component. These interlocking members usually take a hexagonal form, although octagonal forms are also in use. The most common type of dental implant now in use has a hexagonal post or boss (commonly called a "hex") on its gingival end which is adapted to mate with a cooperating six-sided or twelve-sided socket on a restoration component.

Dental implants are available in a variety of styles. One style is designed to install the implant substantially entirely within the patient's jawbone with its hex accessible subgingivally at the crest of the jawbone. Another style of implant incorporates a transgingival section and is installed with that section extending through the gingiva overlying the site of the implant installation. This is often referred to as a "single-stage" implant. Thus, its interlocking member is generally within or above the gingiva.

After installation, the implant is left in position for several months until it becomes integrated within the patient's jawbone (i.e. osseointegration). With the subgingival style of implant, the implant is covered by the patient's fleshy gum tissue during the osseointegration period. Thereafter, in a second stage surgery, the gum tissue is typically opened to expose an end of the implant, and a component having a transgingival section (typically called a healing abutment) is attached to the implant until the surrounding gum tissue heals around the component. After the gum tissue has healed, the transgingival component is removed to expose the interlocking member on the end of the implant, which is thereafter available to connect with a cooperating member of a dental restoration or restoration component. With the single-stage implant, a healing abutment is generally not used because the patient's gum tissue heals around the transgingival section of the implant during osseointegration. Hence, osseointegration and gingival healing in a single-stage implant occur in one, or a "single stage."

It is sometimes desirable to convert one style of implant to another style. For example, if one style is best suited for installation in a first site in a patient's jawbone, but another style is best suited for installation in another site, the restoring dentist seeking to fashion a bridge supported on implants installed in both sites might prefer to convert one style to the other in order to make a bridge using common components. Similarly, if a restoring dentist has on hand implants of one style and components for a new improved style become available, for reasons of economy it might be desirable to convert the available implants to the new styles so they can be used with the new components. Such conversion may be achieved by fitting selected transition components over the interlocking members of the respective implants, thereby forming a "converted" implant. An exemplary set of transition components is described in PCT Publication No. WO 99/17676, assigned to the assignee of the present invention and incorporated herein by reference. "Converted" implants, like "regular" implants, generally include an interlocking member at their occlusal end for mating with a cooperating surface of a prosthodontic restoration (i.e. artificial tooth) or restoration component. These interlocking members may take any form provided in a dental implant, including, for example, hexagonal or octagonal posts or sockets.

With either style of implant, or with "converted" implants, the process of fashioning the restoration usually begins with the step of attaching an impression coping to the implant and making a dental impression of the implant's site where the impression coping is affixed and of the adjacent teeth. The coping normally includes an interlocking member which will anti-rotationally connect with the interlocking member of the implant (or "converted" implant). Thus, for example, where the implant (or "converted" implant) has a six-sided "hex" post, a coping having a hexagonal or 12-point socket may be positioned on the post. A coping with a hex socket may be positioned on a hex post in only one of six possible orientations, sixty degrees apart. A finer adjustment may be achieved by using a coping fitted with 12-point sockets, which can be installed on a hex post in any one of twelve orientation positions that are thirty degrees apart.

After the coping is attached to the implant and the impression taken, the impression is removed from the patient's mouth so that it may be used to make a stone model of the patient's case. In one technique using a "pick-up" type impression coping, the coping is automatically "picked up" (i.e. removed from the implant) during removal of the impression material. In another technique using a "transfer" type impression coping, the coping remains attached to the implant during removal of the impression material, but is then removed from the implant by the clinician and "transferred" back into the impression material. Thereafter, an implant analog is attached to the coping, preferably in the exact orientation as the implant (or "converted" implant), and the stone model is made. The implant analog normally includes the same type of interlocking member as the implant itself. Thus, for example, where the implant has a six-sided "hex" post, the implant analog will normally also have a hex post. In such case, where a coping having a 12-point socket is used in the impression stage, the implant analog may be installed in the coping in any one of twelve orientation positions that are only thirty degrees apart.

One of the most important aspects of a successful restoration is that the restored tooth must be pleasing in appearance when positioned within the patient's mouth. The aesthetic aspect of the dental restoration is particularly important when a single anterior (i.e. front) tooth is being restored. Not only must a front tooth look natural at the gum line, but it must align naturally with the two adjacent teeth. A single restored tooth must neither project forward, recede rearward nor be "twisted" around the axis of the underlying implant in relation to the adjacent teeth. To that end, it is important that the orientation of the implant analog in the stone model is exactly the same as the orientation of the actual implant (or "converted" implant) in the patient's mouth. This normally requires that, in the impression stage, the connecting means on the implant analog is perfectly aligned with the connecting means on the implant (or "converted" implant) itself. If, for example, the hex of an implant analog is not perfectly aligned relative to the hex of an implant in the impression stage, a restored tooth fashioned on the implant analog will be misaligned relative to the patient's teeth, when attached to the implant in the patient's mouth.

Perfect alignment of the implant and implant analog is difficult to achieve, however, especially when impression copings having 12-point sockets are used. This is because the dentist is not able to see clearly the actual orientation of the hex of the implant analog within the 12-point socket of the impression coping. Moreover, the dentist can not reliably note the position of implant hex itself because the end hex of the implant (or "converted" implant) is quite small (about 2–3 mm between parallel flat surfaces) and can be buried relatively deeply below the gingival tissue. One of the aspects of the present invention is directed to solving or at least reducing the effects of this problem by providing a method and device for more easily orienting the implant analog with the dental implant (or "converted" dental implant) at the impression stage.

SUMMARY OF THE INVENTION

In accordance one aspect of the present invention, there is provided a method for positioning an implant analog within a dental impression taken from a patient having a dental implant, the dental implant having a gingival end that is accessible through an opening in the patient's gingival tissue and that includes an interlocking member adapted to receive a dental restorative component thereon. The method comprises the steps of first attaching an impression coping to the implant. The impression coping includes an interlocking member dimensioned to interconnect with the interlocking member on the implant. Then, impression material is applied to the patient to obtain a dental impression when the impression coping is attached to the implant. Next, the dental impression is removed from the patient, a body portion of the impression coping being imbedded within the dental impression and the interlocking member of the impression coping being accessible through an opening in the impression material. An implant analog is then attached to the impression coping. One end of the implant analog includes an interlocking member that is substantially the same as the interlocking member on the implant. Another end of the implant analog includes reference means, usually a physical marking on the surface, in alignment with at least a portion of the interlocking member on the implant analog. The implant analog is positioned on the impression coping in the impression material in such a way that the reference means reaches a selected alignment position.

The selected alignment position of the implant analog preferably is a mirror image of the alignment position of the implant itself. This may be achieved by attaching an orientation tool to the interlocking member of the implant in the patient's mouth. The orientation tool includes implant reference means, also a physical marking on the surface, corresponding in orientation to the interlocking member of the implant. The restorative dentist observes the orientation of the implant reference means and rotates the implant analog to a position on the impression coping, which is still within the impression material, where the implant analog reference means is oriented in a mirror image relative to the implant reference means.

In accordance with another aspect of the present invention, there is provided a set of dental components for use in making a dental impression of a patient having a dental implant. The set of dental components comprises an impression coping, an implant analog and an orientation tool. The impression coping includes an interlocking member dimensioned to interconnect with a dental implant having a cooperating interlocking member. The implant analog includes at one end an interlocking member substantially the same as the interlocking member on the implant and adapted to interconnect with the interlocking member of the impression coping. The implant analog includes at another end implant analog reference means in alignment with at least a portion of the interlocking member on the implant analog. The orientation tool includes at one end an interlocking member adapted to interconnect with the interlocking member on the implant and at another end implant reference means in alignment with at least a portion of the interlocking member on the orientation tool.

BRIEF DESCRIPTION OF THE DRAWINGS

In the drawings, which comprise a portion of this disclosure:

FIG. 1b is a perspective view of the upper portion of the dental implant shown in FIG. 1a;

FIGS. 2a–2c is a side, bottom, and top view, respectively, of an orientation tool which may be used to determine the orientation of a dental implant in the jaw of a dental patient according to one aspect of the present invention;

DETAILED DESCRIPTION

Figure 1A:
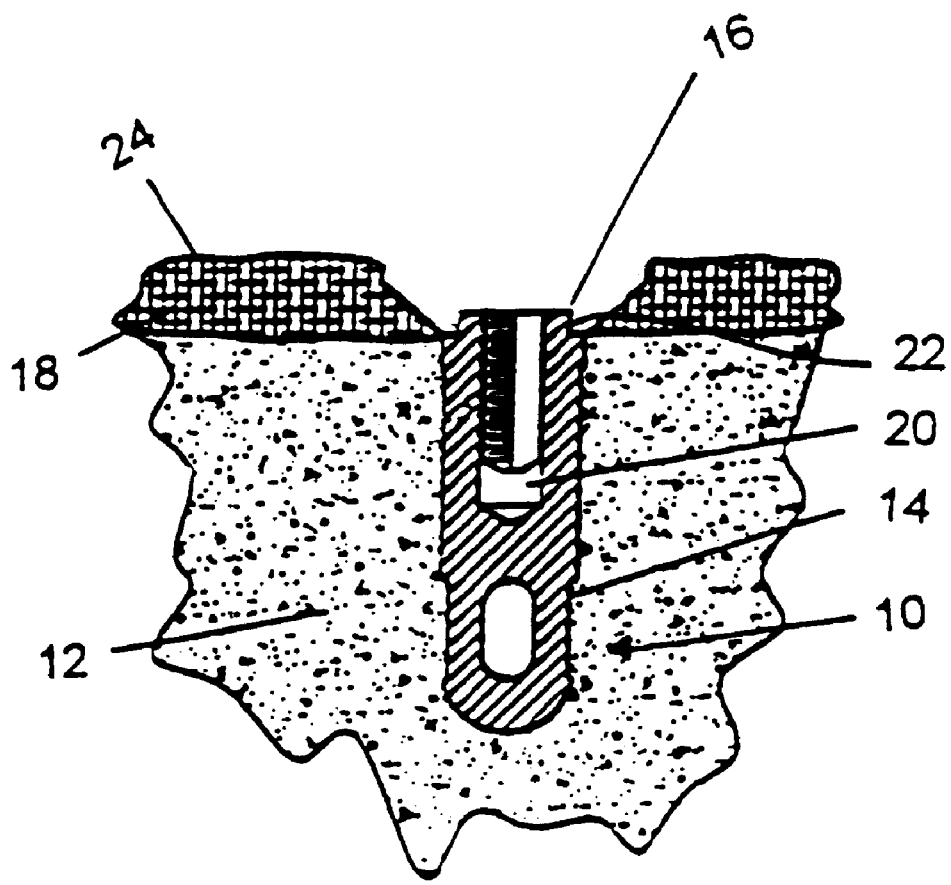
FIG. 1a is a cross sectional view of an implant of the subgingival style in the jaw of a dental patient.
Figure 1B:
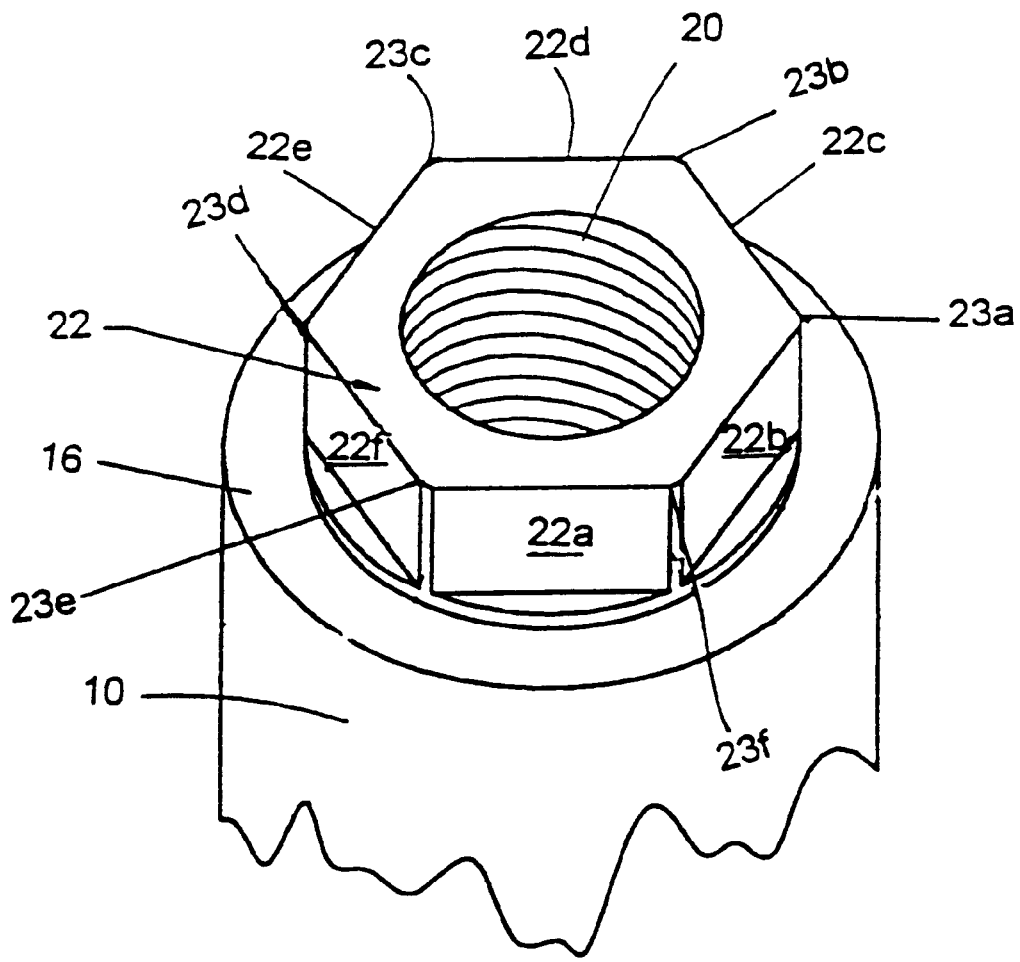

FIGS. 1a and 1b illustrate a subgingival style dental implant 10 implanted in the jawbone 12 of a dental patient. The implant 10 includes a substantially cylindrical base portion 14 which is inserted into the patient's jawbone 12 in the location of the natural root of the lost tooth. A gingival end 16 of the implant 10 extends upwardly from the jawbone 12 and is accessible through an opening in the patient's gingival tissue 18. An internally threaded bore 20 extends through the implant 10 to facilitate attachment of the implant 10 to an abutment or dental restorative component.

As can be best observed in FIG. 1b, the gingival end 16 of the implant 10 comprises a hexagonal post 22 defined by six rigid and generally flat external sidewalls 22a through 22f meeting in corners 23a through 23f. The sidewalls are generally parallel to a longitudinal axis of the implant 10. It will be appreciated, however, that the gingival end 16 of the implant may comprise a socket rather than a post. The hexagonal post 22 (or socket) is adapted to receive and interlock with a mating end of a dental restorative component which may comprise, for example, a healing abutment, impression coping or artificial tooth.

Where the gingival end 16 of the implant comprises a hexagonal post, the mating end of the dental restorative component typically comprises either a hexagonal or twelve-sided socket adapted to receive and interlock with the post. Conversely, where the gingival end 16 of the implant comprises a socket, the mating end of the dental restorative component typically comprises a post adapted to be inserted into and interlock with the socket. Although the posts and sockets will hereinafter be described as having polygonal cross sections, it will be appreciated that they may be designed in any type of non-round cross-sectional shape adapted to interlock with a corresponding mating part.

Figure 1C:
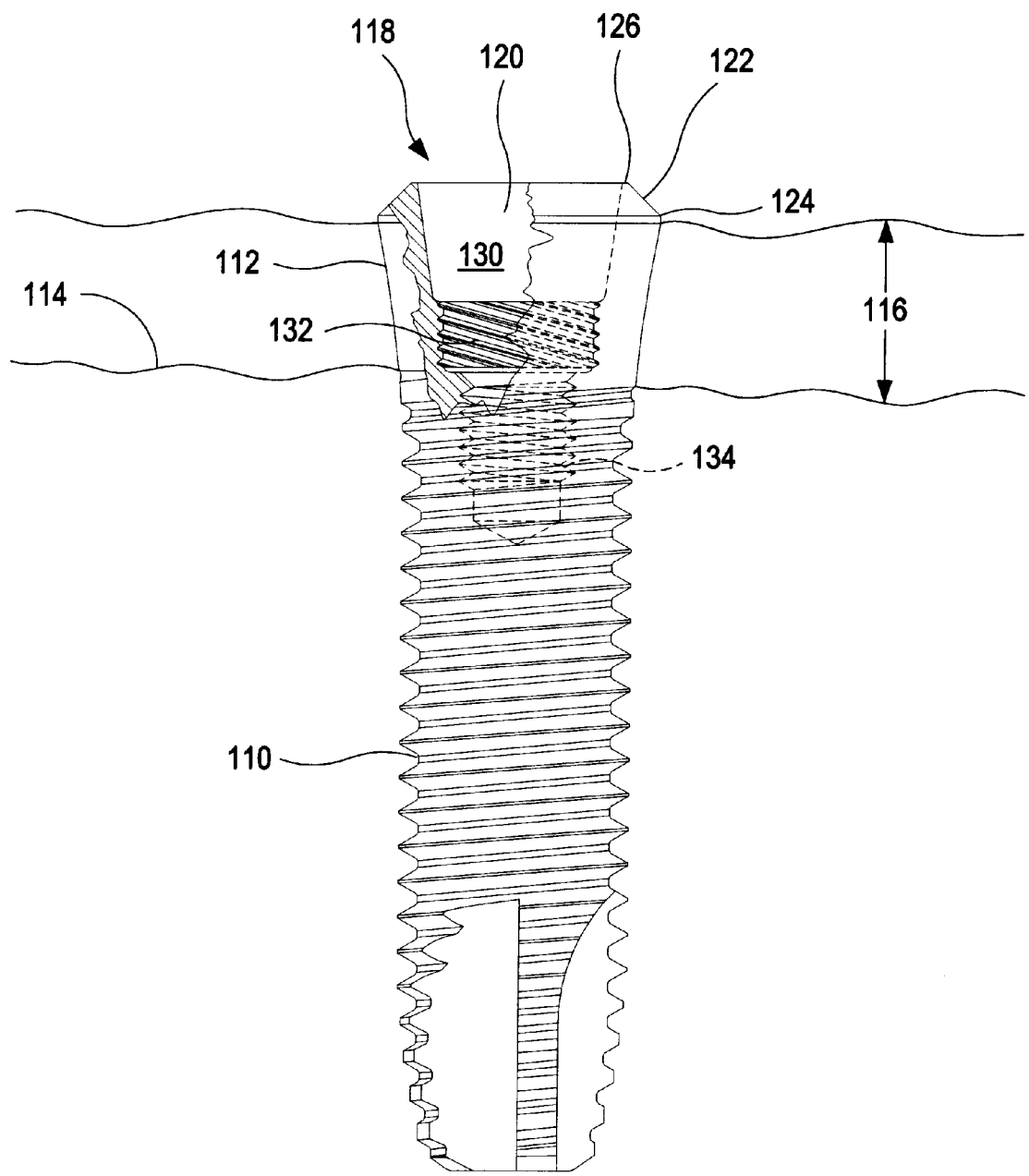
FIG. 1c is a side elevation, partially in section, of a single-stage implant having a transgingival section.

FIG. 1c illustrates one style of a single-stage dental implant 110 implanted in the jawbone 114 of a dental patient. The implant 110 has a transgingival section 112 extending above the bone crest 114 and through the overlying gum tissue 116. The occlusal end 118 of the implant 110 is exposed above the gum tissue 116 and has a central bore 120 opening through it. The end surface of the implant 110 includes a beveled surface 122 angled downward toward the gum tissue 116 from the bore 120 to a periphery 124. A small flat annular surface 126 remains between the beveled surface 122 and the bore 120.

The bore 120 has three zones 130, 132 and 134, proceeding in sequence from the annular surface 126 into the interior of the implant 110. An inwardly tapering, outermost zone 130 is followed by a substantially cylindrical, intermediate zone 132 which, in turn, is followed by an internally threaded, innermost zone 134. The innermost zone 134 is internally threaded for receiving a bolt used to attach components to the implant 110. The intermediate zone 132 is cylindrical on a diameter larger than that of the innermost zone 134. The surface of this intermediate zone 132 is largely or wholly cylindrical; and the outermost zone 130 flares on an angle, suitable for a locking taper, from the intermediate zone 132 to the annular surface 126.

The inside surface of the cylindrical intermediate zone 132 has four shallow, widely spaced threads for receiving a corresponding multiple-lead threaded surface on a attachment component, such as a carrier, which is assembled with the implant and delivered to the clinician in this manner. Because of the spacing and dimension of the threads, a portion of the cylindrical wall of the zone 132 remains intact as it forms the lands between adjacent threads. In one embodiment of the implant 110, the axial length of the cylindrical zone 132 is slightly greater than 1 mm, and the pitch of the threads is about 1 mm. Thus, a single turn of a screw or other component threadably mating with the wall of the zone 132 will serve to insert or remove that screw or other component.

Figure 1D:
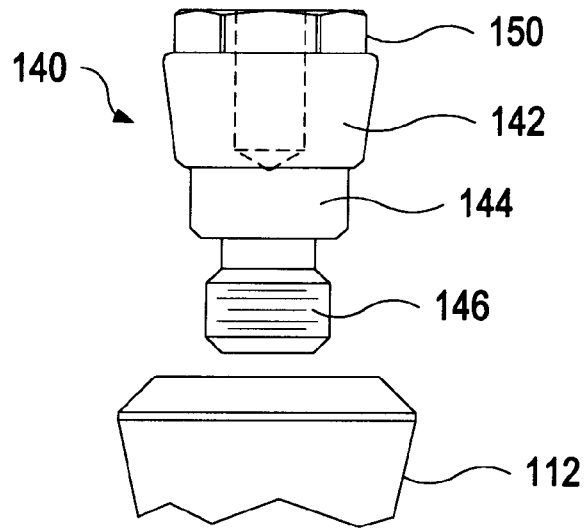
FIG. 1d is an exploded side elevation view, partially in section, of a transition component for use with a single-stage dental implant.
Figure 1E:
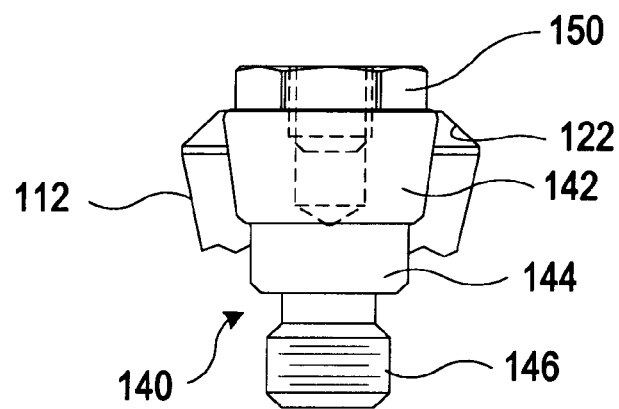
FIG. 1e shows the transition component of FIG. 1d attached to a single-stage dental implant.

Referring now to FIGS. 1d and 1e, there is shown a transition component 140 having a lower section designed to fit into the implant of FIG. 1c. This lower section includes a tapered zone 142, an intermediate zone 144 and an externally threaded zone 146 designed to fit in the corresponding zones 130, 132 and 134 of the implant bore 120. Specifically, the threaded zone 146 screws into the innermost zone 134 of the implant 110, the intermediate zone 144 mates with the intermediate zone 132 of the bore 120, and the tapered zone 142 seats in the outermost zone 130 of the implant bore 120. A locking taper is formed by the engaging side walls of the zones 130 and 142, and thus only a short thread section 146 is needed on the distal end of the transition component 140.

An upper section of the transition component 140 includes a hexagonal post 150 for anti-rotationally connecting to a mating component such as an abutment, impression coping or artificial tooth. It will be appreciated that the transition component may be fashioned with other non-rotational structures. For example, the transition component 140 may be fashioned with an octagonal post, a hexagonal or octagonal socket, or otherwise any type of non-round cross-sectional shape adapted to mate with a corresponding mating component.

Figure 1F:
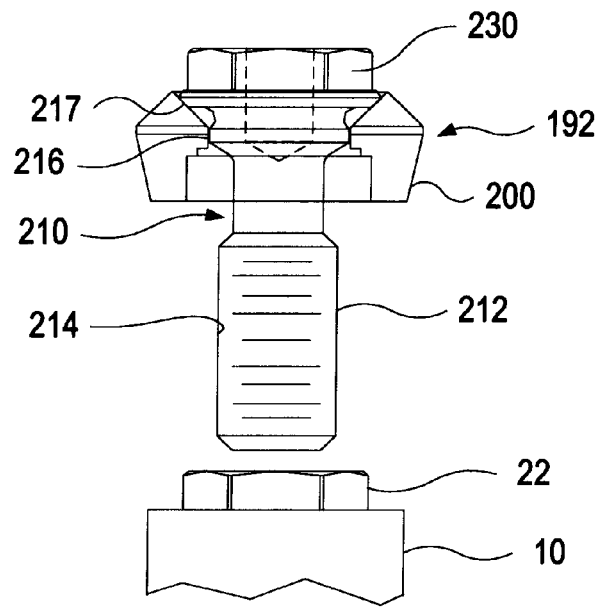
FIG. 1f is an exploded side elevation view, partially in section, of a transition component for use with a subgingival style dental implant.
Figure 1G:
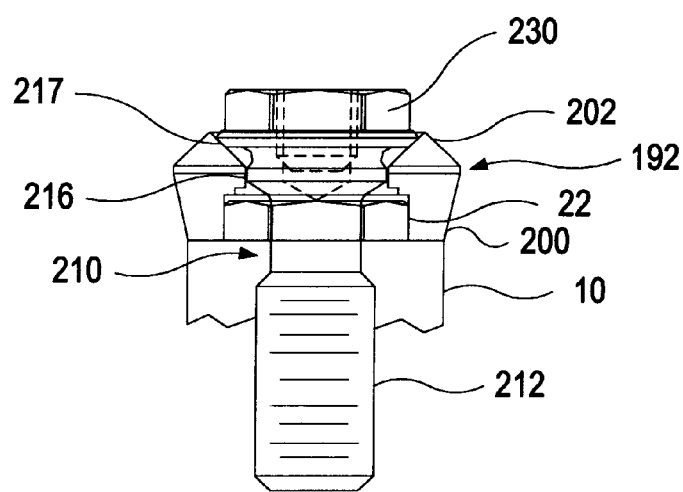
FIG. 1g shows the transition component of FIG. 1f attached to a subgingival style dental implant.

FIGS. 1f and 1g show a form of transition component designed to convert a subgingival type of implant (e.g. implant 10 in FIGS. 1a–1b) to a single-stage implant. The transition component includes an abutment ring 192 fitted non-rotationally over the interlocking member 22 (e.g., hexagonal post) of the subgingival implant 10. Alternatively, the abutment ring 192 may be fashioned to fit non-rotationally over a subgingival implant 10 having a hexagonal socket or other form of interlocking member. The abutment ring 192 has an exterior side surface 200 that mimics the side surface of the transgingival section 112 of the single-stage implant 110 shown in FIGS. 1c through 1e, and a sloping top surface 202 which mimics the sloping top surface 122 of the single-stage implant 110.

An abutment screw 210 attaches the abutment ring 192 to the implant 10. The screw 210 has a threaded stem 212 which engages the threaded bore of the implant 10. Above the stem 212, cylindrical and tapered head sections 216 and 217, respectively, engage corresponding interior surfaces of the abutment ring 192. The portion of the screw head that projects above the abutment ring 192 is a hexagonal post 230 identical to that described above, for anti-rotationally connecting to a mating component such as a healing abutment, impression coping or artificial tooth. Alternatively, the portion of the screw head projecting above the abutment ring 192 may comprise an octagonal post, a hexagonal or octagonal socket, or otherwise any type of non-round cross-sectional shape adapted to mate with a corresponding mating component.

Whatever type of implant or transition is employed, it is preferred that the interlocking members on the implant or transition and/or the mating part will include anti-rotation means projecting from its sidewalls toward the sidewalls of the other interlocking element, as described in U.S. patent application Ser. No. 08/451,083, assigned to the assignee of the present invention and incorporated herein by reference. As described in the referenced application, the anti-rotation means are designed so that the post will fit loosely into the socket upon initial penetration and then more tightly to form an anti-rotational connection upon full penetration. Nevertheless, it will be appreciated that the present invention is applicable to dental components either having or not having anti-rotation means.

FIGS. 2a–2c portray an orientation tool 26 which may be used to orient the interlocking member (e.g., hexagonal post) of the implant 10 during the impression stage. The orientation tool 26 comprises an elongated shaft 28 (FIG. 2a) having an engagement end 30 and an alignment end 32. As can be seen more clearly in FIG. 2b, the engagement end 30 includes a hexagonal socket 34 having six internal sidewalls 34a through 34f which are adapted to engage with the external sidewalls of a hexagonal post 22 of the implant 10. The engagement end 30 of the orientation tool 26 may include anti-rotation means of the type described in U.S. patent application Ser. No. 08/451,083 to form an anti-rotational connection with the implant 10. Alternatively, the engagement end 30 may include a hexagonal post for engaging with an implant having a hexagonal socket, or the engagement end 30 may include an octagonal post or socket or generally any alternative type of interlocking member and/or anti-rotation means.

As can be best observed in FIG. 2c, the alignment end 32 is connected to a hexagonal alignment head 36 having six external sidewalls 36a through 36f. The alignment head 36 is larger than but has the same axial orientation as the hexagonal socket 34 (or post) on the engagement end 30 of the tool 26. A reference groove 38 extends across two opposing corners of the hexagonal alignment head 36. Alternatively, the reference groove 38 may comprise a line painted or etched into the alignment head 36, or the line or groove may be positioned on the side rather than the top of the alignment head 36. As will be appreciated by those skilled in the art, the alignment head 36 may include any of several alternative reference means, but preferably will comprise at least one flat surface in alignment with a corresponding two opposing flat surfaces of the underlying post or socket. Thus, for example, where the underlying post or socket on the engagement end 30 of the tool 26 has an octagonal shape (to mate with an implant or "converted" implant having a hexagonal interlocking element), the alignment head 36 may include eight sidewalls or other reference means which in have the same axial orientation as the underlying post or socket.

The orientation tool 26 may be used according to one embodiment of the present invention to note the orientation of the underlying hexagonal post or socket of the implant during the impression stage, after the implant has osseointegrated with the patient's jawbone. Such use of the orientation tool 26 will be described in detail in relation to FIGS. 9 and 10. To fully understand the use of the orientation tool 26, however, an understanding of the various steps of the impression stage is required and will hereinafter be provided with reference to FIGS. 3 through 8. It will be appreciated that the steps shown in FIGS. 3 through 8 are exemplary only, and relate to the steps used with a subgingival style implant with a hexagonal post, and attaching thereto a specific set of components. The present invention is not limited to the components shown in FIGS. 3 through 8, but may be used with other types of implants (e.g., single-stage or "converted" implants), with other types of interconnecting means, or with other types of components.

Figure 3:
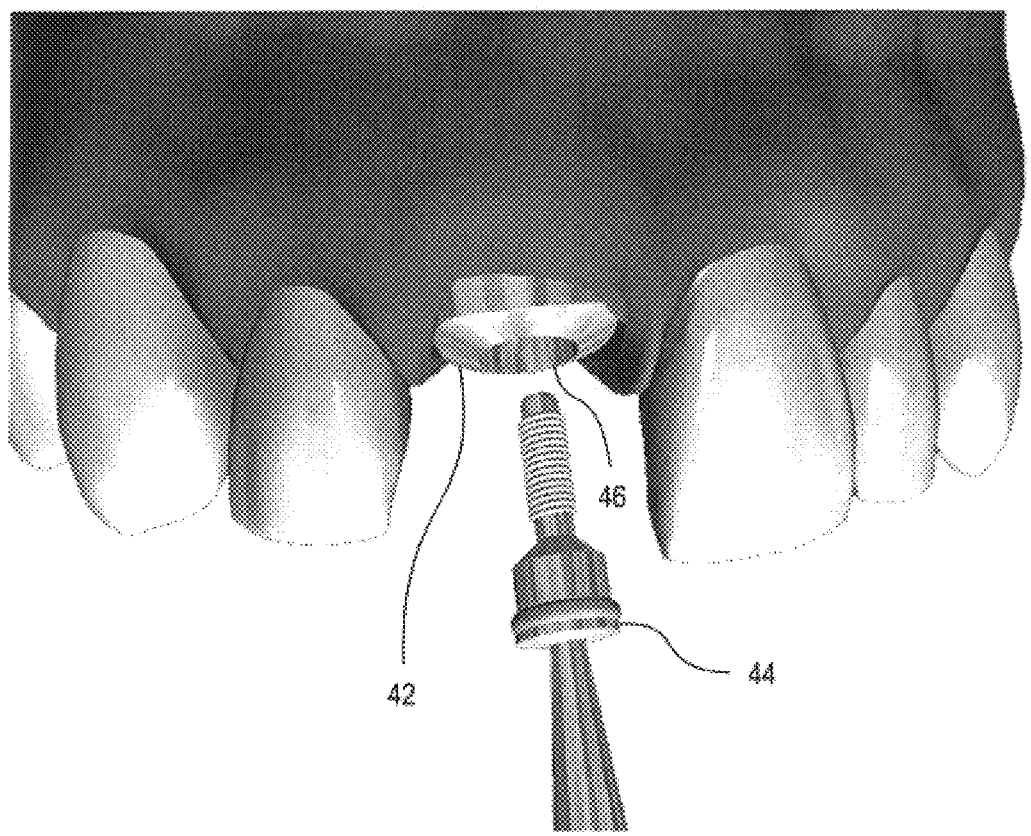
FIG. 3 is a perspective view of a healing abutment within a patient's mouth.

Turning first to FIG. 3, there is shown a healing abutment 42 in the mouth of a dental patient, connected to a subgingival style implant (not visible in FIG. 3) by means of a retaining screw 44. The retaining screw 44 is threadably engaged within the internal bore 20 of the implant, as is known in the art. The healing abutment 42 is normally attached to the implant in a second stage surgery, after the implant has osseointegrated within the patient's jawbone. After second stage surgery, the healing abutment 42 is normally left in place for about six to eight weeks so that the gum tissue heals around the healing abutment. In the illustrated embodiment, the healing abutment 42 has a non-round shape designed to match the anatomical contours desired in the replacement tooth. This type of healing abutment 42 is described in detail in application Ser. No. 08/789,413, entitled "Combined Healing Abutment and Impression Coping," assigned to the assignee of the present invention and incorporated herein by reference in its entirety.

Figure 4:
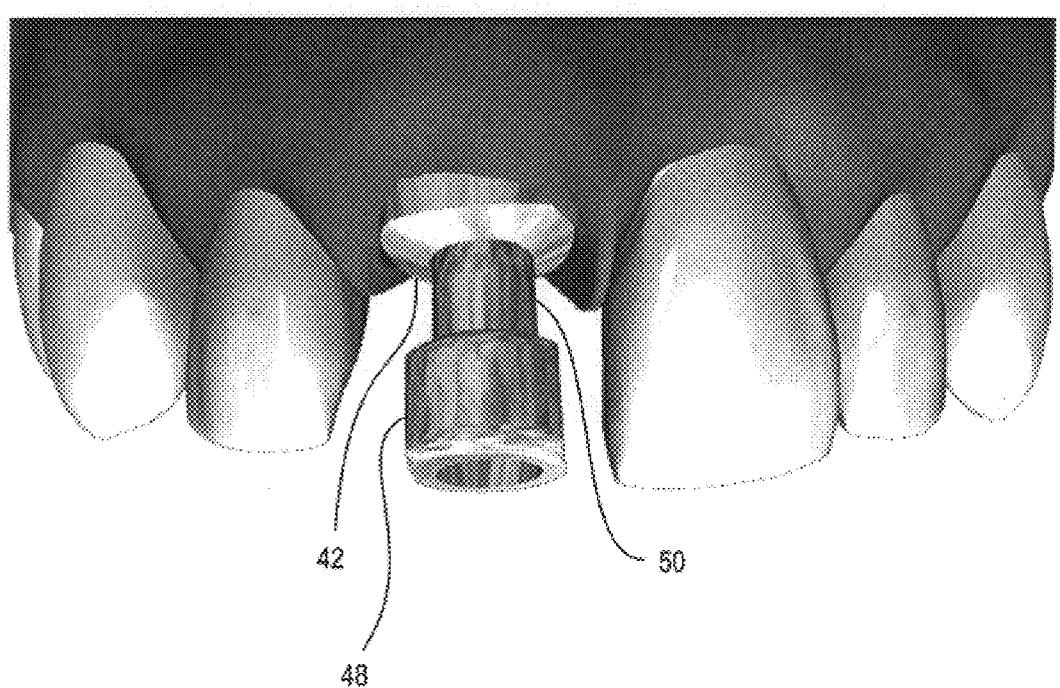
FIG. 4 is a perspective view of a pick-up type impression coping inserted into the healing abutment of FIG. 3.
Figure 5:
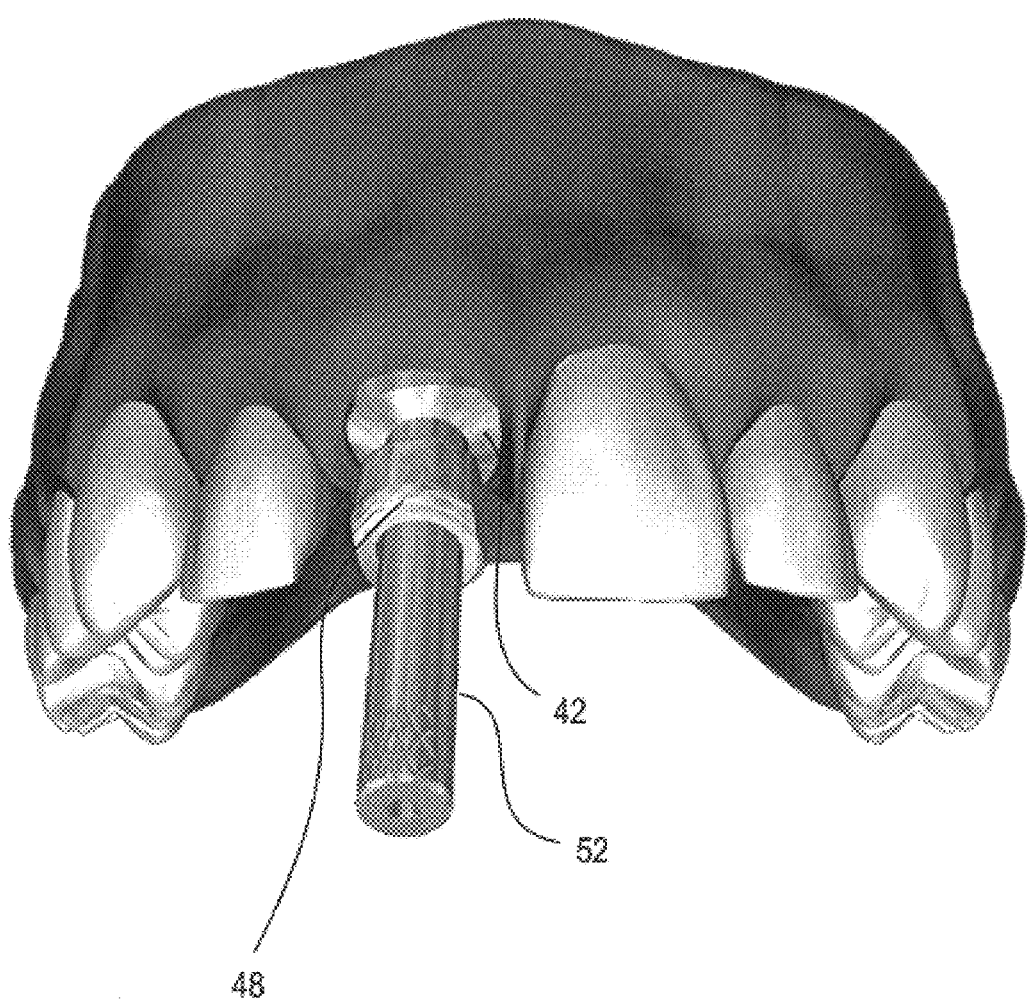
FIG. 5 is a perspective view illustrating an impression pin for securing the pick-up type impression coping and healing abutment of FIG. 4 to an implant.

After the healing abutment 42 has been in position for the appropriate length of time, the retaining screw 44 is removed to expose a tapered internal bore 46 of the healing abutment 42. Next, as shown in FIG. 4, an impression coping 48 having a tapered end 50 is inserted into the internal bore 46 of the healing abutment 42. The internal bore 46 of the healing abutment and the tapered end 50 of the impression coping each are slightly tapered (e.g. about 2 to 3 degrees) to facilitate a tight frictional engagement between the impression coping 48 and the healing abutment 42. The healing abutment 42, being frictionally engaged with the impression coping 48, thus forms a part of the impression coping as described further in the incorporated U.S. patent application Ser. No. 08/789,413. Thereafter, as shown in FIG. 5, the impression coping 48 and healing abutment 42 are secured to the implant 10 with an impression pin 52. The impression pin 52 has a threaded stem (not visible in FIG. 5) which engages the internally threaded bore of the underlying implant.

Figure 6:
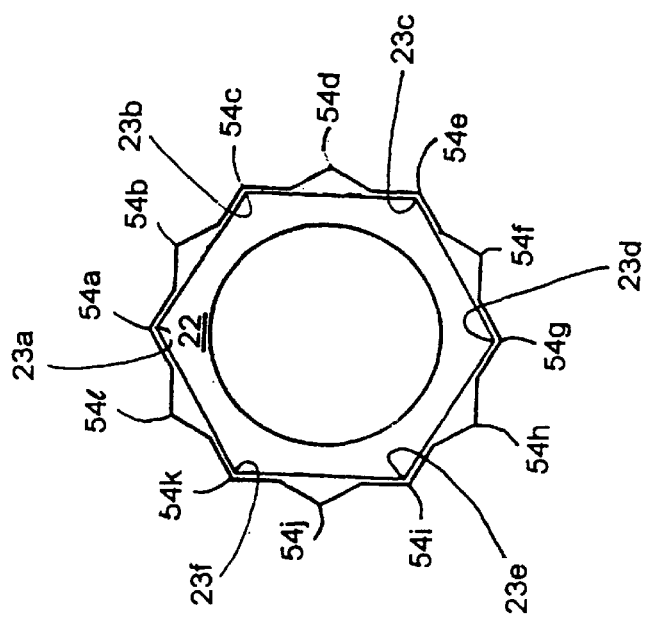
FIG. 6 is a cross sectional view illustrating the interconnection of a six-sided post with a twelve-sided socket.

The impression coping 48 includes a mating end (not visible in FIG. 4 or 5) comprising a socket adapted to interconnect with the hexagonal implant post. In one embodiment, the mating end of the impression coping 48 comprises a twelve-sided socket adapted to interconnect with the hexagonal implant post in any one of twelve orientation positions, each thirty degrees apart. A cross-sectional view of the interconnection of a six-sided post into a twelve-sided socket is shown in FIG. 6. In an alternative embodiment, the mating end of the impression coping 48 includes a six-sided socket for interconnecting with a hexagonal implant post. Alternatively, the impression coping 48 may include either a six-sided or twelve-sided post for interconnecting with a hexagonal implant socket, or may otherwise include any type of interconnecting element adapted to anti-rotationally engage with the dental implant (or "converted" implant).

As shown in FIG. 6, the six corners 23a through 23f of the post 22 are engaged within every other corner of twelve corners 54a through 54l of the socket 54. Thus, the implant post 22 may be oriented within the socket 54 in any one of twelve orientation positions, each 30 degrees apart. In an embodiment (not shown) where the impression coping has a six-sided socket, the implant post 22 may be oriented in any one of six orientation positions, each sixty degrees apart.

Figure 7:
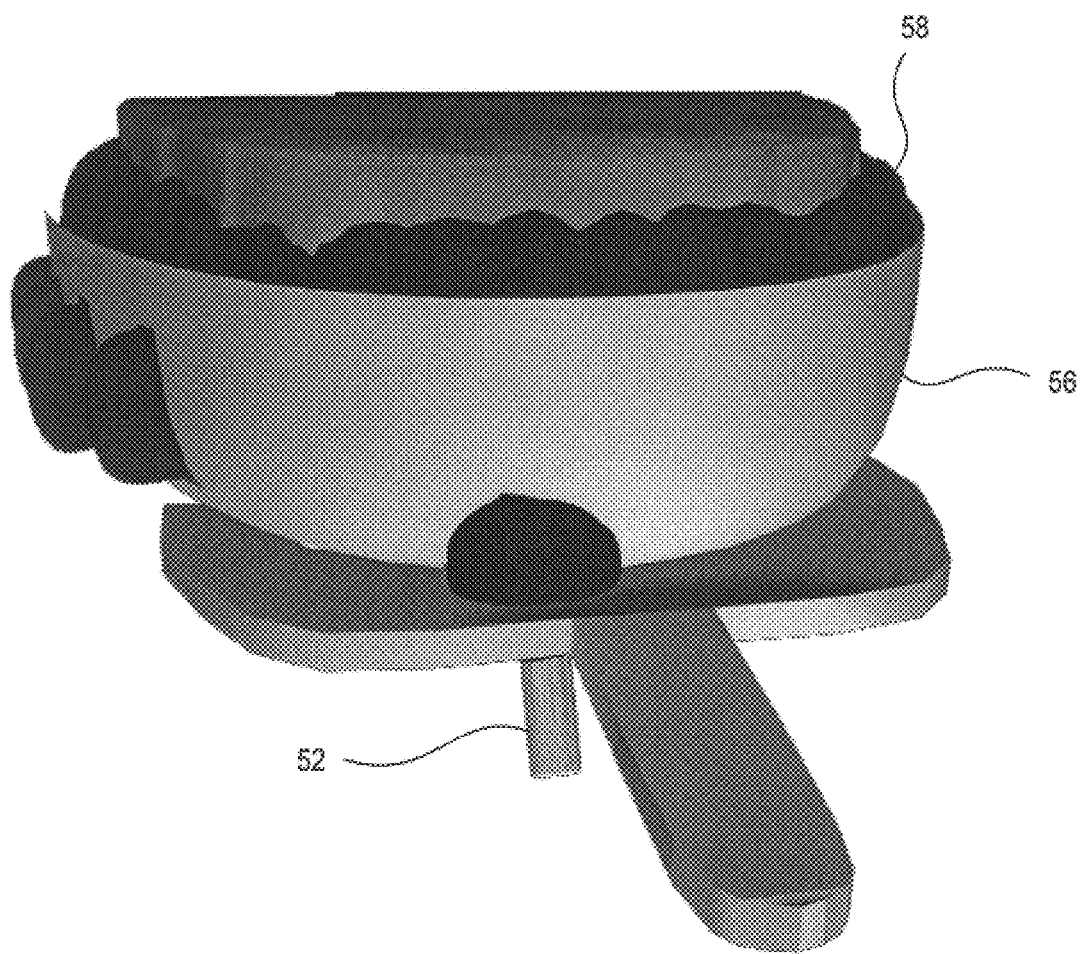
FIG. 7 is a view of an impression tray interaction with the impression coping of FIGS. 4–5.

After the impression coping 48 is secured within the healing abutment 42 with an impression pin 52 as shown in FIG. 5, a dental impression is made in the usual manner, by inserting a mouthpiece containing resilient impression material as shown in FIG. 7. The impression material forms an impression of the patient's teeth which may be removed from the patient's mouth and used to make a stone model of the patient's teeth.

In one technique using a "pick-up" coping, the coping is automatically "picked up" (i.e. removed from the implant) during removal of the impression material. This can be accomplished by providing a larger diameter head on the impression coping (as in coping 48) under which impression material will flow so as to "pick-up" the entire coping when the impression material is removed from the patient's mouth. In another technique using a "transfer" coping, the coping remains attached to the implant during removal of the impression material, but is then disengaged from the implant by the clinician and installed back into the impression material. The coping represented in FIGS. 5 and 6 comprises a pick-up coping, which becomes imbedded in the impression material and removed from the patient upon removal of the impression. The coping represented in FIG. 8 is a transfer coping which is not removed with the impression material, but is "transferred" back into the impression material outside of the patient's mouth after it is disengaged from the implant.

Figure 8:
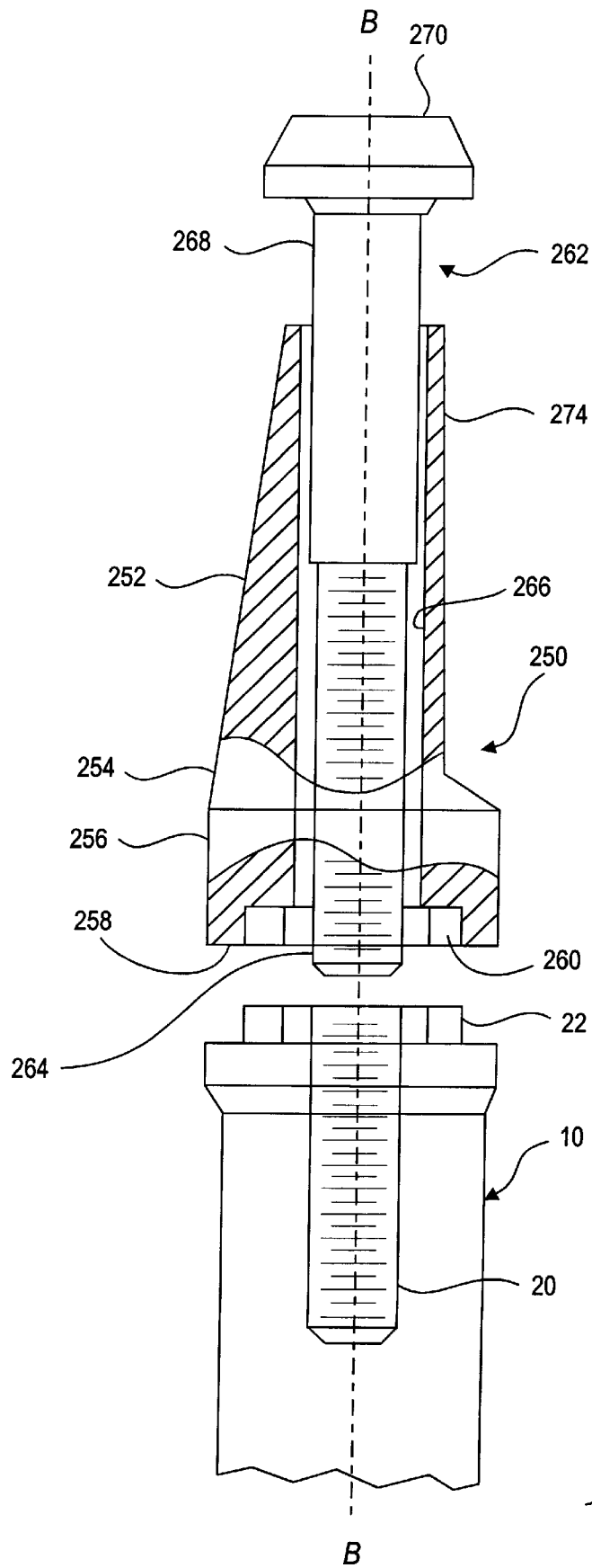
FIG. 8 is an exploded side elevation view, partially in section, of a transfer type impression coping.

FIG. 8 depicts one form of transfer coping which may be used in the impression stage. The transfer coping 250 has a tapered main body 252, the wider end of which (lower end 254 in the drawing) merges into a transmucosal section 256 having in its bottom surface 258 a female hexagonal socket 260 sized to mate with the male hexagonal socket 22 of the implant 10. Alternatively, the coping 250 may include a male hexagonal socket at its bottom surface for connecting with an implant having a female hexagonal socket, or otherwise may include any interconnecting element adapted to anti-rotationally connect with an implant. The coping is attached to the implant 10 with a bolt 262 having at one end a threaded shaft 264 sized to mate with the internally threaded socket 20 of the implant 10. The coping has a bore 266 of a uniform internal diameter running through it, and the bolt has a main shaft 268 of slightly smaller diameter sized to fit within this bore 266. A manipulating head 270 is fixed to the upper end of the main shaft. The threaded shaft 264, of smaller diameter, is fixed to the lower end of the main shaft. The coping 250 has on its tapered section 252 a flattened surface 274 to provide memory or orientation around the axis B—B after the impression is taken.

In use with a subgingival style of implant, the coping 250 is attached directly to the implant 10 with the transmucosal section 256 passing through the gum tissue. The bolt head 270 is tightened on the upper narrow end of the main body 252 with the socket 260 embracing the hex post 22 of the implant. With the coping thus non-rotationally attached to the implant, an impression of the coping and the axially symmetrical bolt head is taken to the surface of the gum tissue. The impression is then removed from the patient's mouth, and then the coping is detached from the implant 10 and transferred to the impression material. Because of the flattened surface 274, the transfer coping 250 can be reinserted into the impression in the precise position since the impression has a corresponding internal flat surface. It should be noted that the transmucosal section 256 can be non-round to fit within a gingival aperture that has been formed by a non-round healing component. It should also be noted that the impression coping 48 can be made to have a taper on its exterior surface allowing it to be used as a transfer-type impression coping.

Figure 9:
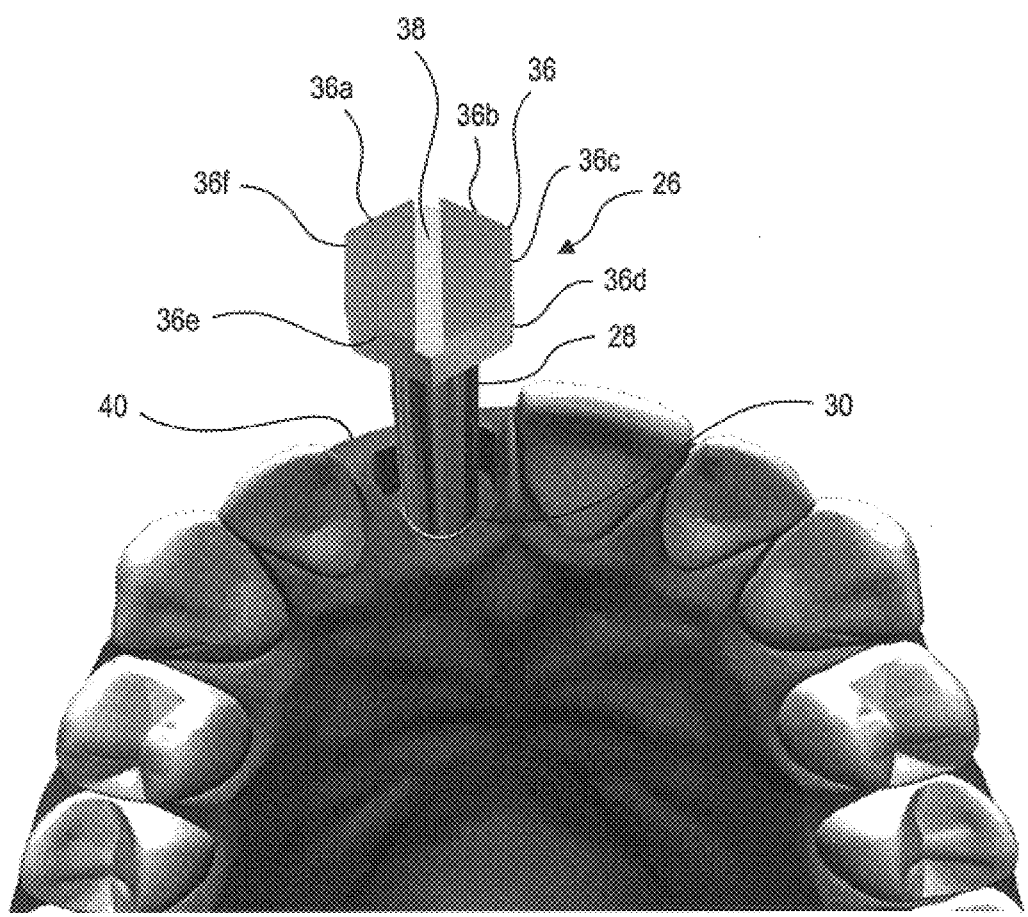
FIG. 9 is a perspective view illustrating the appearance of the dental implant in a patient's mouth after the taking of a dental impression and the removal of the impression coping and healing abutment.
Figure 10:
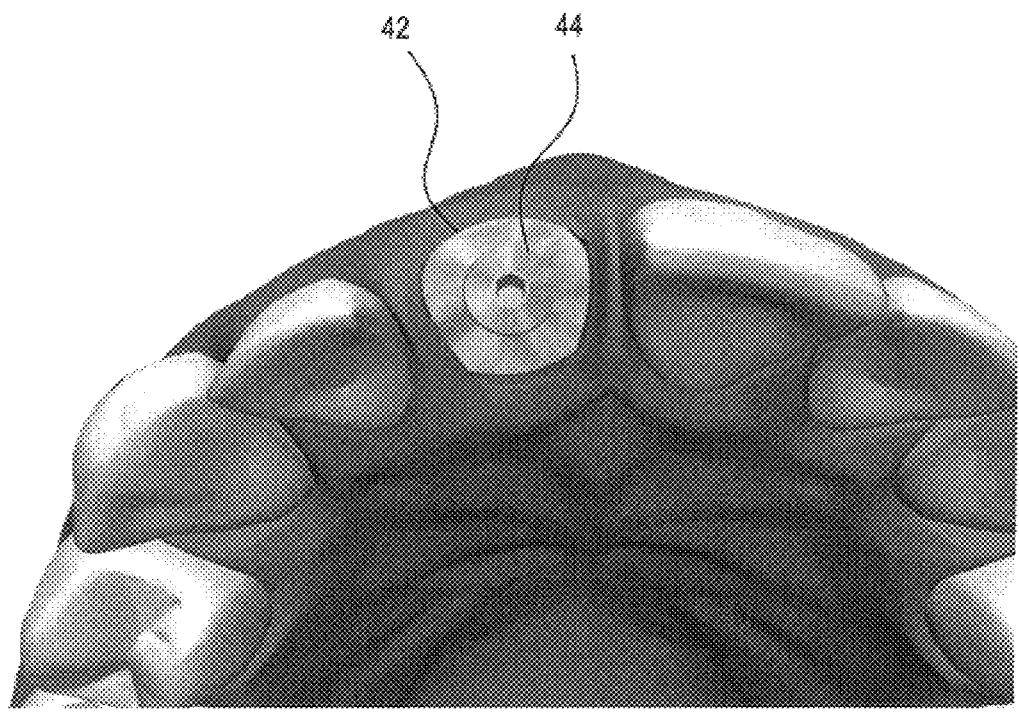
FIG. 10 is a perspective view of the orientation tool of FIGS. 2a–2c connected to the implant of FIG. 9.

Upon removal (e.g., pick-up or transfer) of the impression coping from the patient's mouth (FIG. 9), access is provided to the hexagonal post 22 of the implant 10 through the patient's gum tissue which has healed in a non-round shape approximating the contours of a natural tooth. Then, as depicted in FIG. 10, the orientation tool 26 described in relation to FIGS. 2a–2c may be used to note the orientation of the hexagonal post 22 on the implant, which otherwise would be difficult to observe because of its small size and its position below the gingival tissue. As will be described in relation to FIG. 12, orientation of the implant hex is necessary to achieve proper alignment of the implant analog on the impression coping that is positioned within the impression material.

Orientation of the implant hex is achieved by first engaging the implant with the engagement end 30 of the tool 26, by interlocking the internal sidewalls 34a through 34f of the socket 34 with the external sidewalls 22a through 22f of the implant post 22. Because the alignment head 36 of the orientation tool 26 is oriented in the same axial position as the underlying post 22 on the implant, the clinician may easily note the position of the implant hex by simply observing the position of the alignment head 36 or reference groove 38 on the tool. Each of the sides 36a through 36f of the alignment head 36 in FIG. 10 are oriented in the same axial position as one of the sides 22a through 22f of the underlying implant post 22.

In a preferred embodiment of the present invention, the alignment head 36 is significantly larger than the implant hex so that it may be more easily observed by the clinician. It will be appreciated, however, that the size of the alignment head 36 may be varied to suit the needs of the user. Moreover, it will be appreciated that the alignment head 36 need not have the same cross-sectional shape as the implant hex 22, but must include at least one reference line or flat surface corresponding to the position of the implant hex 22.

Figure 11A:
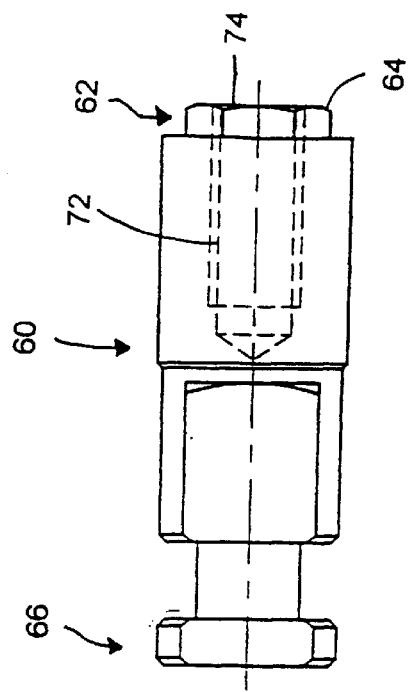
FIGS. 11a and 11b are side and top views, respectively, of an implant analog adapted to be connected to an impression coping imbedded within a dental impression.
Figure 11B:
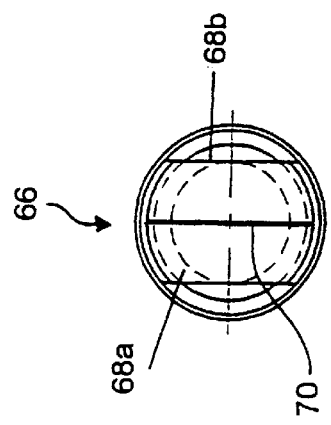

Now turning to FIGS. 11a and 11b, there is shown an implant analog 60 for use with the present invention. The implant analog 60 is attached to the coping (e.g., transfer or pick-up coping), in the impression material, after the impression has been removed from the patient's mouth. A mating end 62 of the implant analog 60 includes an interlocking element having substantially the same configuration and anti-rotational design as the corresponding interlocking element on the implant (or "converted" implant) itself. In the illustrated embodiment, for example, the implant analog has a hexagonal post 64 corresponding to an implant having a hexagonal post (FIG. 9). The hexagonal post 64 is adapted to interconnect with a hexagonal or twelve-sided socket in the impression coping 48. If the interlocking element on the implant itself comprises a hexagonal socket or anything other than a hexagonal post, then the configuration of the interlocking element on the implant analog may correspondingly be changed to match the configuration of the implant itself.

The implant analog 60 includes a head 66 which permits a clinician to note the position of the post 64 or socket of the implant analog when it is engaged within the impression coping socket. As best observed in FIG. 11b, the head 66 includes reference indicator comprising two flat outer surfaces 68a and 68b and a groove 70, each aligned with two opposing flat surfaces of the post 64 on the opposite end of the implant analog 60. As will be appreciated by those skilled in the art, the reference indicator may comprise any of several alternative configurations, but preferably will comprise at least one flat surface in alignment with a corresponding two opposing flat surfaces of the underlying post or socket. For example, rather than a groove 70, the reference means may comprise a line painted or etched into the alignment head 66, or the line or groove may be positioned on the side rather than the top of the alignment head 66. The implant analog further includes an internally threaded bore 72 having an opening 74 adjacent the interlocking hex 64. Like the internally-threaded bore of the implant, the threaded bore 72 is adapted to receive the impression pin 52 to firmly engage the implant analog 60 in the impression coping 48.

Figure 12:
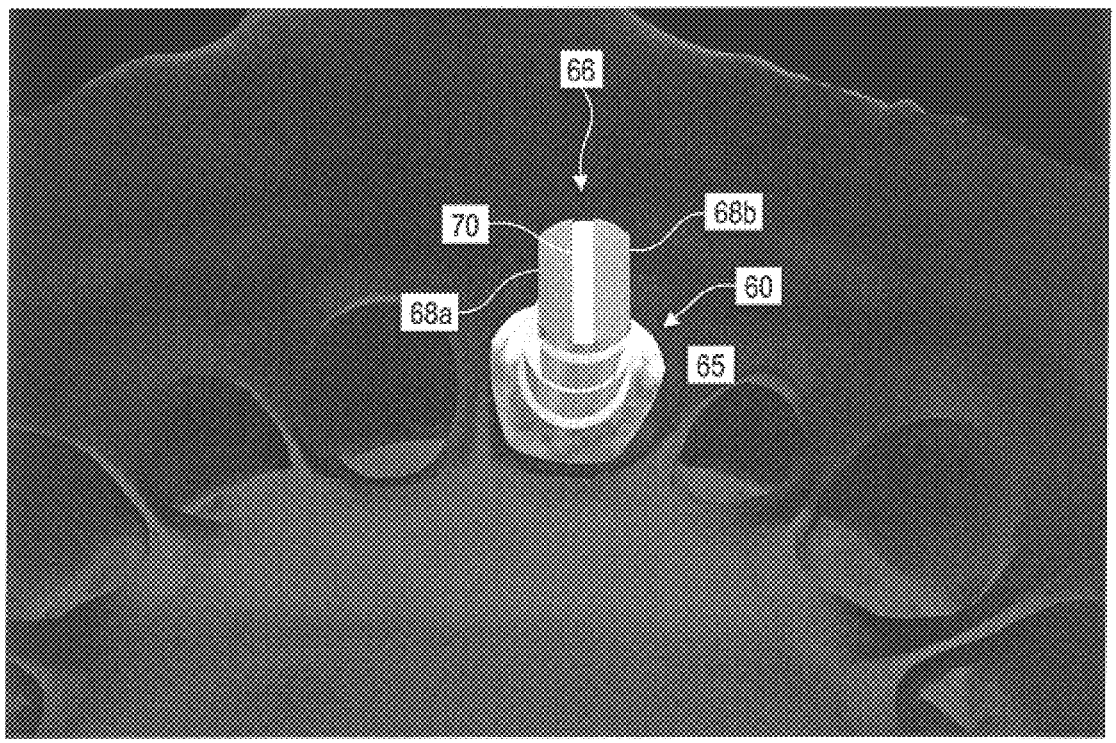
FIG. 12 is a perspective view of the implant analog of FIGS. 11a and 11b attached to an impression coping in the dental impression.

FIG. 12 shows the implant analog 60 with its hexagonal post attached to an impression coping 48 with a twelve-point socket imbedded within the impression material 65. It is noted that neither the hex of the implant analog nor the impression coping is visible at this point in the impression stage. Nevertheless, the present invention provides a reliable method of orienting the implant analog in the dental impression. The reference groove 70 indicates the orientation of the implant analog hex and the alignment tool 26 indicates the orientation of the implant hex. By comparing the reference groove 70 on the implant analog 60 to the groove 38 on the alignment tool 26 in the patient's mouth, the hexagonal post 64 on the implant analog 60 can be aligned with the hexagonal post 22 on the implant (or "converted" implant) in the patient's mouth as will be described in further detail below.

As stated briefly above, the clinician may note the position of the underlying hex 64 of the implant analog 60 by simply noting the position of the reference groove 70 on the head 66 of the implant analog 60. For instance, as shown in FIG. 12, the groove 70 and sidewalls 68a,b on the head 66 of the implant analog 60 are oriented at an angle of about five to ten degrees counterclockwise from a vertical "12 o'clock" position in relation to the dental arch of the patient. Because the reference groove 70 on the head 66 of the implant analog 60 is aligned with the underlying hex 64 of the implant analog 60, the clinician thereby knows that two opposing sides of the underlying hexagonal post 64 are oriented at the same angle as the reference indicator, about five to ten degrees counterclockwise of 12 o'clock. Moreover, the clinician knows from the geometry of the underlying post or socket that the uppermost "flat" of the underlying hex is oriented about five to ten degrees from parallel in relation to the dental arch of the patient.

Figure 13:
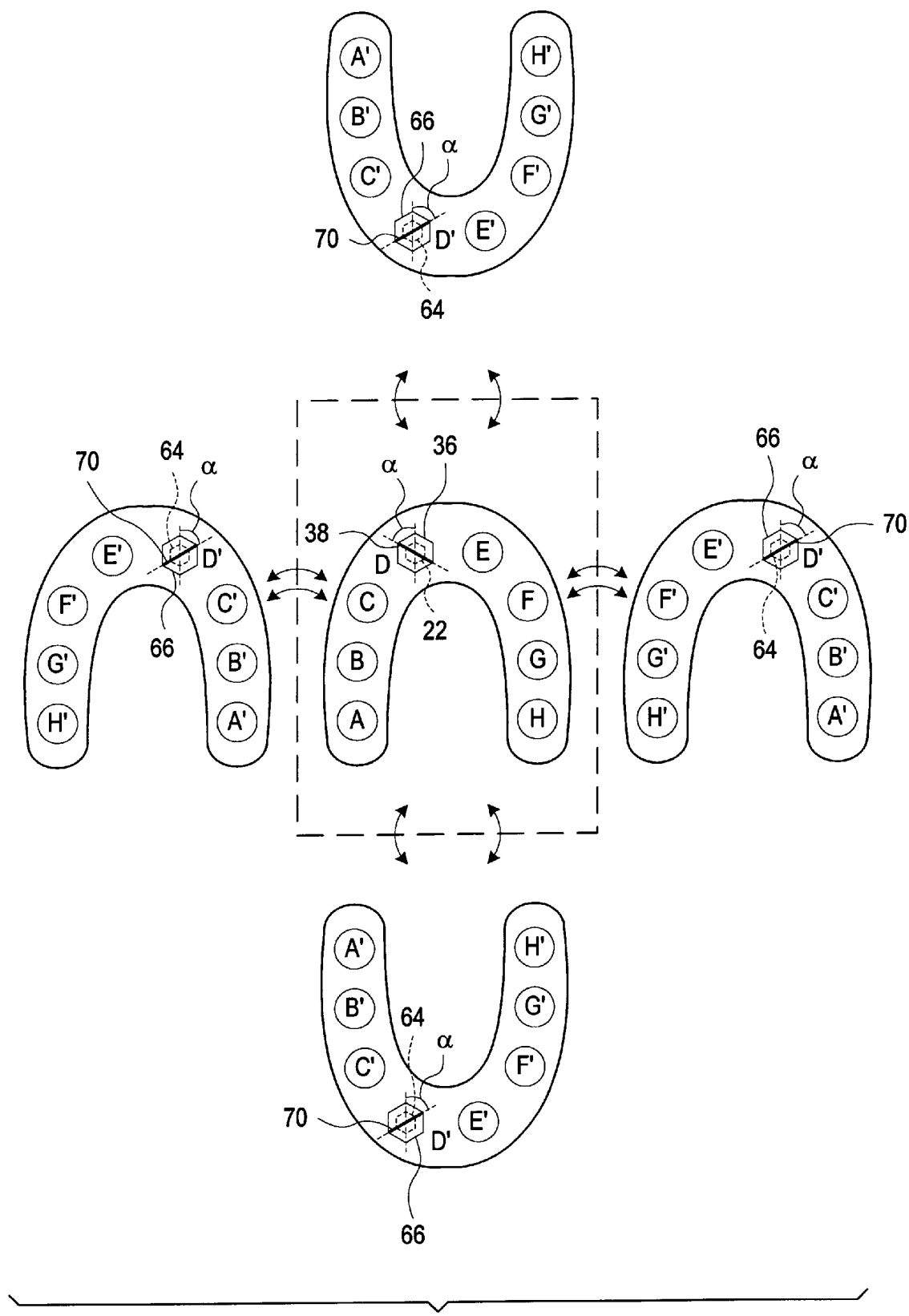
FIG. 13 is an illustration of the comparison of the patient's mouth and the impression that is needed to result in a perfect alignment of the implant and the implant analog.

The clinician observes the position of the hexagonal of the implant (or "converted" implant) by using the alignment tool 26, as described in relation to FIG. 10, and compares the position of the implant with that of the implant analog. FIG. 13 illustrates this comparison that is made by the clinician. The central view of FIG. 13 illustrates the patient's mouth as when, for example, the patient is lying in a dental chair with his or her head tipped back and the clinician is looking at the teeth in the upper jaw. Thus, teeth A–H are actually protruding outwardly from the paper with tooth D being the tooth requiring replacement. The smaller hex is actually the hexagonal post 22 on the top of the implant 10 as is shown in FIGS. 1–2 & 9. The larger hex is the alignment head 36 of the orientation tool 26 as is shown in FIGS. 2 & 10. In FIG. 13, the groove 38 on the alignment tool 26 is at an angle α to the left of a 12 o'clock vertical line.

The other four views represent the view of the impression material after it has been removed from the patient's mouth and the clinician has flipped the impression over in any of the four possible orientations. Tooth depressions A'–H' are the depressions left in the impression material from teeth A–H, as similarly shown in FIG. 12, after the clinician has performed the impression steps previously mentioned. In these four views, the hexagonal post 64 of the implant analog 60 has been inserted into the socket of the impression coping. The head 66 has its alignment groove 70 at the same angle α with respect to the 12 o'clock vertical line. However, the angle α in the impression material is to the right of the 12 o'clock vertical line. In other words, perfect alignment of the implant's hexagonal post 22 and implant analog's post 66 is achieved when the implant analog's position is a "mirror image" of the implant's position relative to a 12 o'clock vertical line. Thus, a "mirror image" orientation is created and, thus, perfect alignment achieved, when the alignment tool's groove 38 is oriented at an angle α on one side of the vertical line, and the implant analog's groove 70 is oriented at the angle α on the other side of the vertical line. The reason for this "mirror image" is that the clinician's line of sight in the central view is with the teeth protruding toward him or her, while in any of the other four impression views the clinician's line of sight is from the reverse side where the teeth are protruding away from him or her. The term "mirror image" and variations thereof shall be construed throughout the present application as being relative to an imaginary vertical line as described above.

If perfect alignment is not observed, the clinician may reorient the implant analog 60 by changing its angular position within the socket of the impression coping until it reaches the perfect alignment position. This reorientation process is accomplished without rotating the impression coping within the impression material. Where the coping socket comprises a 12-point socket, for example, the clinician may reposition the implant analog by rotating it to another of the twelve possible orientation positions in the socket until perfect alignment is achieved. Once perfect alignment is achieved, the implant analog is attached to the impression coping via the impression pin and a stone model of the patient's teeth is made from the dental impression. After the stone model is created, an artificial tooth is fashioned on the stone model. Then, the artificial tooth is attached to the dental implant in the patient's mouth, resulting in a prosthodontic restoration which is virtually perfectly aligned in relation to the patient's adjacent teeth.

While particular embodiments and applications of the present invention have been illustrated and described, it is to be understood that the invention is not limited to the precise construction and compositions disclosed herein and that various modifications, changes, and variations will be apparent from the foregoing descriptions without departing from the spirit and scope of the invention as defined in the appended claims.

What is claimed is:

1. A method for aligning an implant analog within a dental impression taken from a patient having a dental implant, said dental implant having an upper end including an interlocking member adapted to receive a dental restorative component thereon, said method comprising the steps of:

attaching an impression coping to the implant, said impression coping including an interlocking member dimensioned to interconnect with the interlocking member on the implant;

applying impression material to the patient to obtain a dental impression when said impression coping is attached to the implant;

removing the dental impression from the patient, a body portion of the impression coping being imbedded within the dental impression, the interlocking member of the impression coping being accessible through an opening in the impression material;

attaching an implant analog to the impression coping, said implant analog including at one end an interlocking member substantially the same as the interlocking member on said implant, the interlocking member of the implant analog being interconnected with the interlocking member of the impression coping, the implant analog including at another end reference means in alignment with at least a portion of the interlocking member on the implant analog;

attaching an orientation tool to the interlocking member of the implant, said orientation tool including an implant reference means corresponding in orientation to the interlocking member of the implant;

observing the orientation of said implant reference means; and rotating the implant analog until the implant analog reference means mirrors the orientation of the implant reference means.

2. A method for aligning an implant analog within a dental impression taken from a patient having a transition component connected to a dental implant, said transition component having an upper end including an interlocking member adapted to receive a dental restorative component thereon, said method comprising the steps of:

attaching an impression coping to the transition component, said impression coping including an interlocking member dimensioned to interconnect with the interlocking member on the transition component;

applying impression material to the patient to obtain a dental impression when said impression coping is attached to the transition component;

removing the dental impression from the patient, a body portion of the impression coping being imbedded within the dental impression, the interlocking member of the impression coping being accessible through an opening in the impression material;

attaching an implant analog to the impression coping, said implant analog including at one end an interlocking member substantially the same as the interlocking member on said transition component, the interlocking member of the implant analog being interconnected with the interlocking member of the impression coping, the implant analog including at another end reference means in alignment with at least a portion of the interlocking member on the implant analog;

attaching an orientation tool to the interlocking member of the transition component, said orientation tool including an implant reference means corresponding in orientation to the interlocking member of the transition component;

observing the orientation of said implant reference means; and rotating the implant analog until the implant analog reference means mirrors the orientation of the implant reference means.

3. A set of dental components for use in making a dental impression of a patient having a dental implant, said set of dental components comprising:

an impression coping including an interlocking member dimensioned to interconnect with a corresponding interlocking member on the dental implant;

an implant analog including at one end an interlocking member substantially the same as the interlocking member on said implant, the interlocking member of the implant analog being adapted to interconnect with the interlocking member of the impression coping, the implant analog including at another end implant analog reference means for orienting the interlocking member of the implant analog, the implant analog reference means being aligned with at least a portion of the interlocking member on the implant analog; and an orientation tool including at one end an interlocking member adapted to interconnect with the interlocking member on said implant, the orientation tool including at another end implant reference means for orienting the interlocking member of the orientation tool, the implant reference means being aligned with at least a portion of the interlocking member on the orientation tool.

4. The set of claim 3 further comprising an impression pin for securing the impression coping to the implant when making the dental impression.

5. The set of claim 3 wherein the interlocking member of the implant analog and orientation tool comprises a hexagonal post and the interlocking member of the impression coping comprises a twelve-sided socket.

6. The set of claim 3 wherein the interlocking member of the implant analog and orientation tool comprise hexagonal sockets and wherein the interlocking member of the impression coping comprises a twelve-sided post.

7. A set of dental components for use in making a dental impression of a patient having a dental implant and a transition component connected thereto, said set of dental components comprising:

an impression coping including an interlocking member dimensioned to interconnect with a corresponding interlocking member on the transition component;

an implant analog including at one end an interlocking member substantially the same as the interlocking member on said transition component, the interlocking member of the implant analog being adapted to interconnect with the interlocking member of the impression coping, the implant analog including at another end implant analog reference means for orienting the interlocking member of the implant analog, the implant analog reference means being aligned with at least a portion of the interlocking member on the transition component; and an orientation tool including at one end an interlocking member adapted to interconnect with the interlocking member on said transition component, the orientation tool including at another end implant reference means for orienting the interlocking member of the orientation tool, the implant reference means being aligned with at least a portion of the interlocking member on the orientation tool.

8. The set of claim 7 further comprising an impression pin for securing the impression coping to the transition component when making the dental impression.

9. The set of claim 7 wherein the interlocking member of the implant analog and orientation tool comprises a hexagonal post and the interlocking member of the impression coping comprises a twelve-sided socket.

10. The set of claim 7 wherein the interlocking member of the implant analog and orientation tool comprise hexagonal sockets and wherein the interlocking member of the impression coping comprises a twelve-sided post.

* * * * *

UNITED STATES PATENT AND TRADEMARK OFFICE
CERTIFICATE OF CORRECTION

PATENT NO. : 6,135,773
DATED : October 24, 2000
INVENTOR(S) : Lazzara

It is certified that error appears in the above-identified patent and that said Letters Patent is hereby corrected as shown below:

Cover page, [56], Foreign Patent Documents, delete "1911470" and insert
--1291470--

Signed and Sealed this

Twenty-second Day of May, 2001

*Attest:*

NICHOLAS P. GODICI

*Attesting Officer*   Acting Director of the United States Patent and Trademark Office